United States Patent [19]
Lee et al.

[11] 3,994,047
[45] Nov. 30, 1976

[54] APPARATUS FOR THE TWIN-WIRE AIR LAYING OF FIBROUS PADS

[75] Inventors: Charles A. Lee; Frank D. Sorrells, both of Knoxville, Tenn.

[73] Assignee: International Paper Company, New York, N.Y.

[22] Filed: Apr. 11, 1975

[21] Appl. No.: 567,124

[52] U.S. Cl. ............................................. 19/156.3
[51] Int. Cl.² ........................................... D01G 25/00
[58] Field of Search....... 19/88, 89, 155, 156–156.4; 156/62.2, 62.4, 62.8, 63, 231, 232, 243; 425/80–83, 85

[56] References Cited
UNITED STATES PATENTS

| | | | |
|---|---|---|---|
| 2,688,393 | 9/1954 | Uschmann | 19/155 X |
| 3,030,245 | 4/1962 | Greiner et al. | 156/62.8 |
| 3,071,822 | 1/1963 | Meiler | 19/156.3 |

FOREIGN PATENTS OR APPLICATIONS

| | | | |
|---|---|---|---|
| 2,024,038 | 11/1971 | Germany | 19/156.3 |

*Primary Examiner*—Dorsey Newton
*Attorney, Agent, or Firm*—Fitch, Even, Tabin & Luedeka

[57] ABSTRACT

Fibers are air laid on a twin-wire machine to form a composite pad. A pair of endless foraminous carriers are passed through a forming chamber where fibers suspended in air are directed between the carriers. A layer of fibers is built up on each of the carriers by applying pressure differential across the carriers in the chamber to force air from the suspension through the carriers. In one form of the invention the air is directed through the respective carriers in different patterns to form a respective fiber layers of different cross section. The carriers converge within the chamber in their direction of motion to join the facing surfaces of the respective layers to form a composite pad of non-uniform cross section. According to one aspect of the invention, excess fibers are removed from the facing surfaces just prior to their being joined.

6 Claims, 5 Drawing Figures

APPARATUS FOR THE TWIN-WIRE AIR LAYING OF FIBROUS PADS

This invention relates generally to the twin-wire air laying of fibers to form a pad and more particularly, to the laying of such a pad at high speeds. Still more particularly, it relates to the laying of such a pad having a non-uniform cross section. The invention finds particular application in making contoured disposable diapers.

It is well known to form pads of wood fibers by air laying, that is, by directing fibers in an air stream onto a forming carrier, known as a wire, through which the air is withdrawn, collecting a pad of fibers on the carriers. It is known to make such pads in discrete units having a predetermined contour by masking the forming carrier so that the pad is formed on isolated sections of the carrier. It is also known to form a pad having non-uniform cross section by forming a layer of fibers of uniform cross section and then forming on top thereof another layer of different width. The latter practice presents certain difficulties when high speed is desired, as it is difficult to deposit the second layer with uniformity at high speeds by withdrawing air through the first layer. It is known to lay a second layer on the first, but this presents added difficulties in handling the flimsy second layer, as well as requiring duplication of machinery.

The present invention is directed to the high speed twin-wire forming of pads formed as a composite of two layers of uniform thickness which may be of different cross sections and different areas. The two layers are formed on separate forming carriers in a common forming chamber at high speeds. Twin-wire air forming has been known heretofore; however, such apparatus when operated at high speeds frequently resulted in clumps of fiber agglomerating at various places in the final pad, leaving the pad unsuitable for many purposes.

In accordance with the present invention, provisions are made for controlling the formation and correcting for such non-uniformities. In one aspect of the invention, the pressure differential for withdrawing air through the respective forming carrier is increased in the direction of motion of the carriers, assuring that the layers are formed relatively uniformly without substantial shearing forces as might roil the forming webs and produce peaks and valleys therein. In another aspect of the invention, there is provided means operating somewhat like a vacuum cleaner to shear off peaks in the formed webs before the webs on the two forming carriers are joined to form the resulting pad. This corrects for non-uniformity in the webs as formed. Further, the same means removes excess fibers and aberrations as may be occasioned by the forming of webs in discrete units.

It is therefore an object of the invention to provide a simple method and apparatus for forming a pad of air laid fibers at high speeds utilizing two forming carriers to form respective uniform layers of fibers which are joined to form the pad. Another object of the invention is to form a contoured pad. It is a further object of the invention to form such pads in discrete units. Other objects and advantages of the invention will become apparent from the following detailed description, particularly when taken in conjunction with the accompanying drawings, in which.

Figure 1:
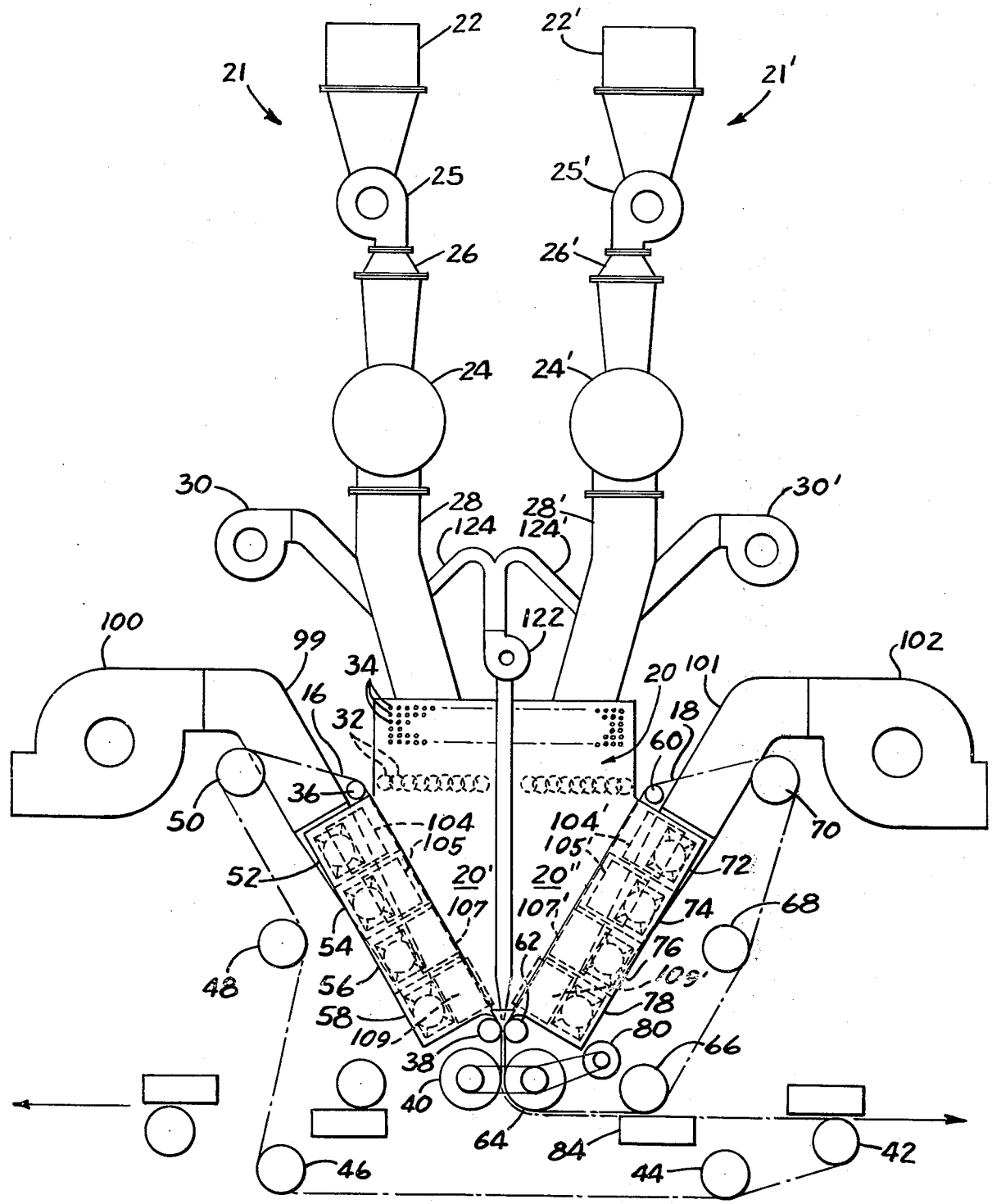
FIG. 1 is a front elevation, partly diagrammatic, of a preferred form of air laying apparatus according to the present invention.
Figure 3:
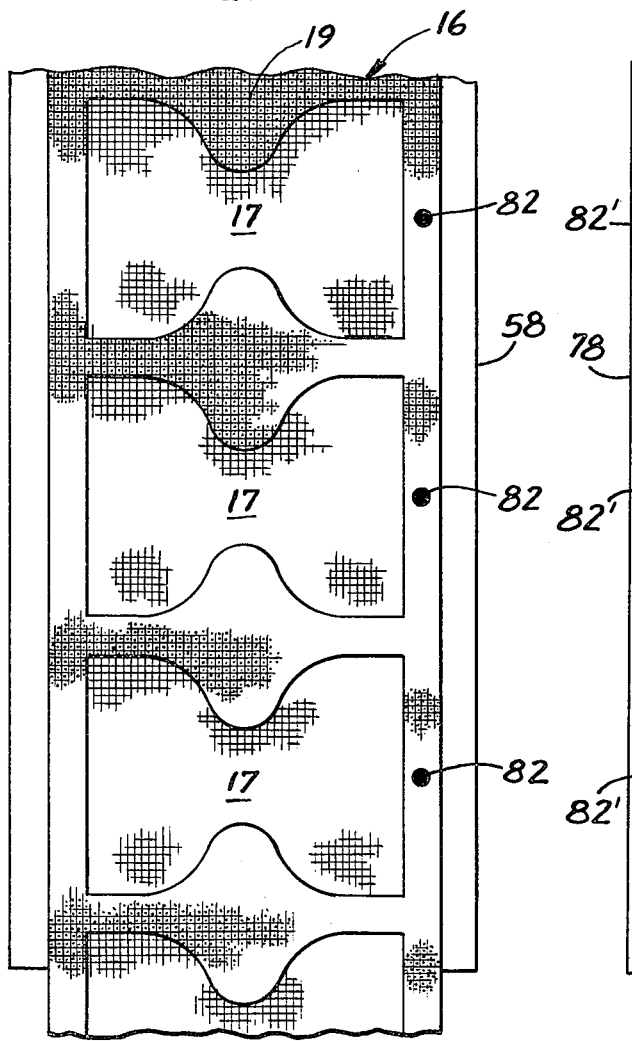
FIG. 3 is a plan view of one form of carrier used in the apparatus of FIG. 1.
Figure 4:
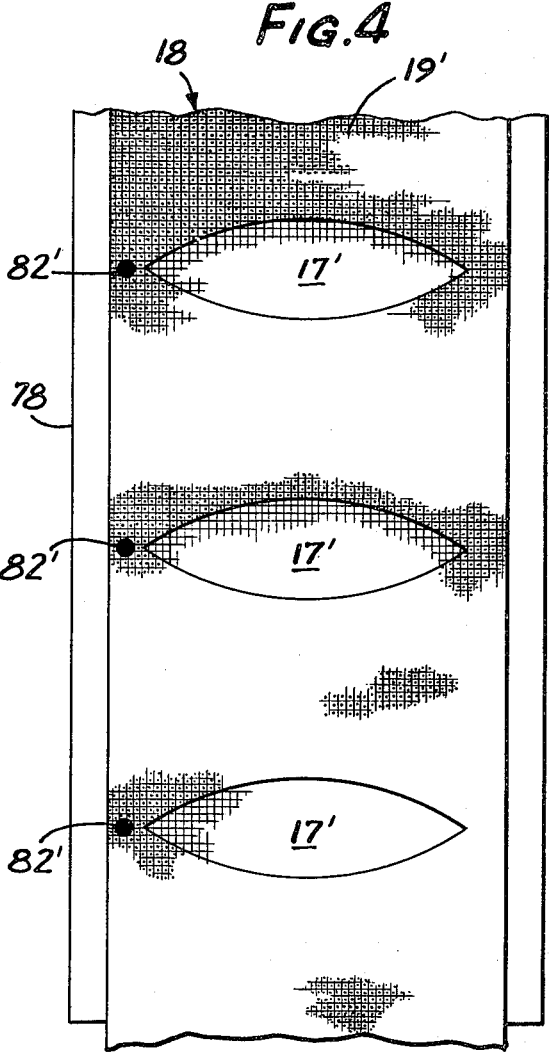
FIG. 4 is a plan view of a form of a carrier complementing that illustrated in FIG. 3.
Figure 5:
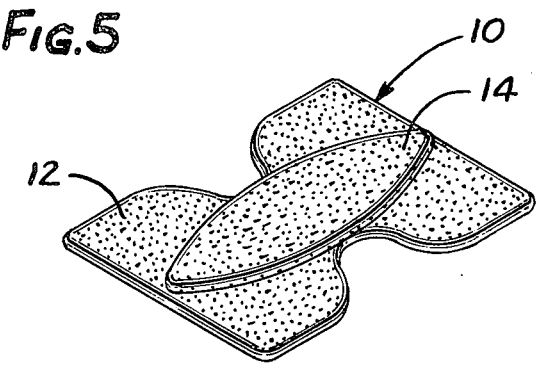
FIG. 5 is an isometric view of a contour pad formed by joining the layers formed using the carriers illustrated in FIGS. 3 and 4.

As shown in the drawings for purposes of illustration, the invention is embodied in an air laying apparatus for making discrete composite pads 10 which may be in the form of the diaper pads illustrated in FIG. 5. Such pads may then be encased in a wrapper, as of crepe tissue and other material, to form finished diapers. The pads 10 are formed simultaneously in the apparatus as illustrated in FIG. 1. In the pads illustrated, the units of one layer, layer 12, are of hourglass shape, and the units of the other layer, layer 14, are ovate. Respective units are formed simultaneously in the machine and are mated symmetrically to form the pads illustrated in FIG. 5. In the apparatus illustrated, the layer 12 is formed on an endless foraminous carrier 16, while the layer 14 is formed on an endless foraminous carrier 18. The layers 12 and 14 are formed on the respective carriers 16 and 18 by depositing fibers from an air suspension as the carriers 16 and 18 pass through a forming chamber 20, the upper separate regions of which are identified as 20' and 20'', respectively As illustrated in FIGS. 3 and 4, the carriers 16 and 18, although sometimes known as wires, are preferably made of woven synthetic material, forming screens having foramina providing an appropriate air permeability while blocking the passage of most of the fibers in the air stream. The foramina are left open in the areas 17 and 17' where the layers are to be built up but are blocked to make them suitably air impermeable over the remaining region 19 and 19', respectively. The blocking material must be flexible and compatible with the material forming the carriers 16 and 18. Such material is silicone rubber.

The pad is preferably formed of individual fibers of wood pulp, as those produced by the divellication of webs of felted wood pulp. As illustrated, there may be two divellicating units 21 and 21', each comprising a shredder 22 and 22' and a refiner 24 and 24'. Each shredder 22 accepts a web of wood pulp and breaks it up to small pieces, for example less than an inch square. These pieces fall into a respective blower 25 and 25' which drives them through a respective chute 26 or 26' into a respective refiner 24 or 24'. Each refiner 24 may be a conventional refiner for breaking up the pieces into separate wood fibers. The individual fibers then pass through respective chutes 28 and 28' into the forming chamber 20, the blowers 25 and 25' driving the fibers downward suspended in an air stream. At the same time, blowers 30 and 30' provide additional air for driving the fibers and facilitating their suspension in the air stream. Within the forming chamber 20, additional means, which may take the form of toothed discs 32 known as whizzers rotated in the air stream, may be used to stir up the suspended fibers to maintain sufficient turbulence to assure the relatively uniform suspension of the fibers as they fall through the forming chamber 20 onto the respective forming carriers 16 and 18. As may be desirable, additional air may be admitted to the forming chamber 20 through controlled openings 34 in the wall forming the chamber 20.

The forming carrier 16 is supported by rolls 36, 38, 40, 42, 64, 46, 48 and 50 for movement over a path into the forming chamber 20, over a plurality of successive suction boxes 52, 54, 56 and 58, and thence out of the forming chamber. At the same time, the carrier 18 is supported by rolls 60, 62, 64, 66, 68 and 70 for movement into the forming chamber 20, over a plurality of suction boxes 72, 74, 76 and 78, and thence out of the forming chamber. The forming carriers 16 and 18 are driven at the same speed by a motor 80. The rolls 48 and 68 may be tension rolls which may be adjusted to provide the appropriate tension in the respective forming carriers 16 and 18 as may be required, for example, to keep the carriers in registration with each other. To this end, the respective forming carriers 16 and 18 may have registration indicia 82 and 82'. These indicia may be sensed, as by an electric eye, to indicate any misregistration, and in response to such indication the appropriate tension roll 48 or 68 may be adjusted to maintain registration.

As illustrated, the carriers 16 and 18 are supported by the respective suction boxes to follow converging paths within the forming chamber 20. The respective layers 12 and 14 are air laid on the carriers as the carriers pass over the respective suction boxes. The carriers 16 and 18 with their respective layers 12 and 14 come together at the exits, joining the facing surfaces of the layers 12 and 14 to form the pad 10. The pad is carried between the carriers 16 and 18 around the roll 64. The carrier 18 is then removed around the roll 66, with a suction box 84 being utilized to hold the formed pad 10 to the carrier 16. The pad is thereafter removed from the carrier 16 for further processing in any desired manner, as by wrapping it to form a diaper.

Figure 2:
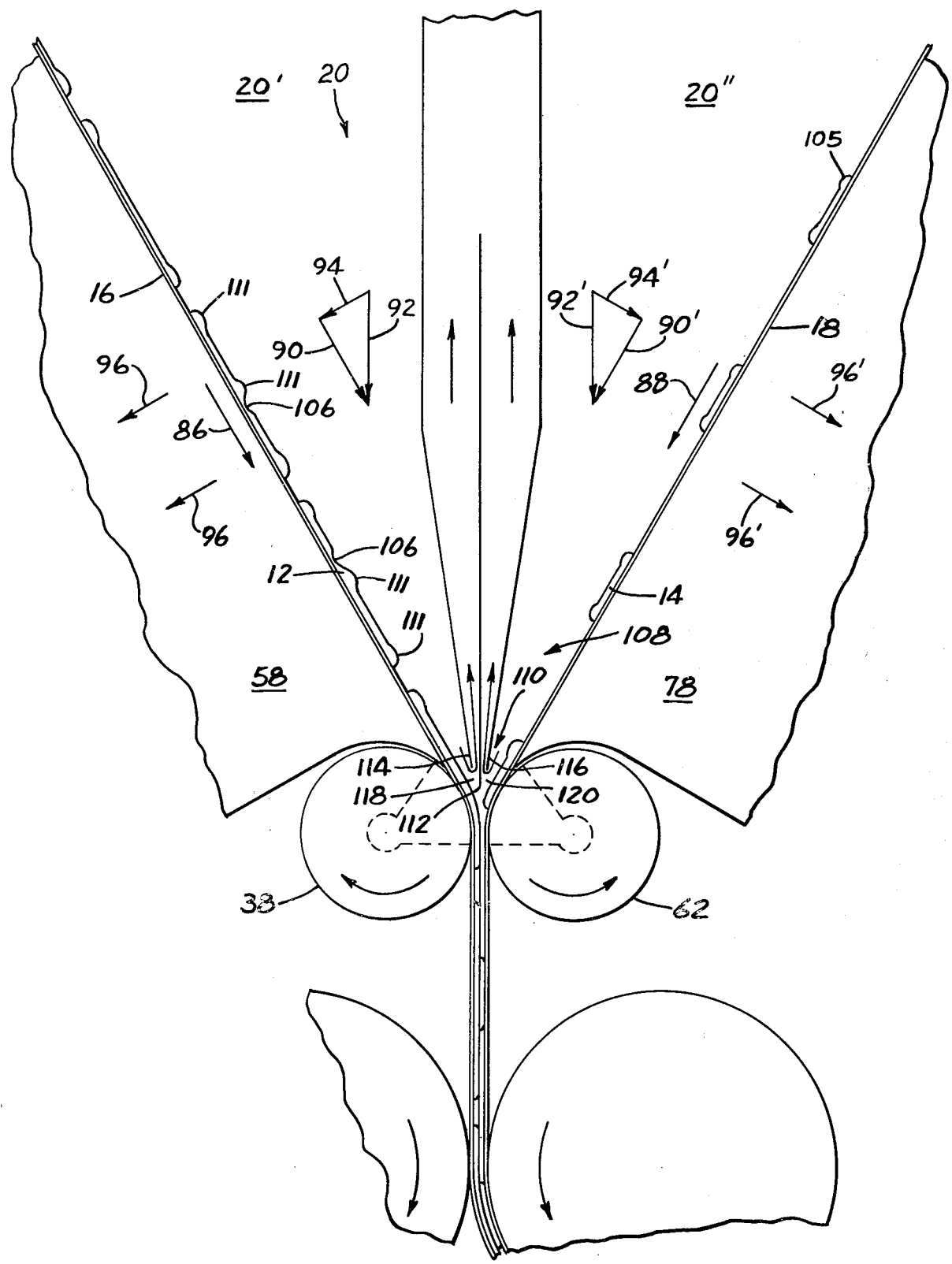
FIG. 2 is an enlarged sectional view partly diagrammatic, of part of the apparatus shown in FIG. 1, showing particularly the terminal portion of the forming chamber.

As mentioned above, it is important that the layers 12 and 14 be laid down in an orderly manner and retained in place without disruption. To this end, the flow of the suspended fibers in the chamber 20 is coordinated with the movment of the carriers 16 and 18 through the chamber as well as with the withdrawal of air from the suspension through the carriers 16 and 18. The relationships are illustrated in FIG. 2, where the various arrows indicate both direction and velocity, their length indicating velocity. It is contemplated that the apparatus operate with carriers 16 and 18 moved by the rolls 38 and 62 at a rate of 1200 feet per minute, as may be indicated by the arrows 86 and 88. For uniform deposition of the respective layers 12 and 14, it is desirable that the fibers suspended in the air flowing through the chamber 20 have a component of velocity in the direction of the respective carriers 16 and 18 substantially equal to the speed of the carriers. This component is indicated by the arrows 90 and 90', the total velocity of the suspension being indicated by the arrows 92 and 92'. The suspension therefore has a component of velocity normal to the carriers 16 and 18 as indicated by the arrows 94 and 94'. Again, in order to avoid roiling the layers 12 and 14, the air carrying the fibers against the respective carriers 16 and 18 should be removed as it reaches the carriers, with the webs of fibers being built up on the respective carriers as fast as the air-borne fibers arrive, as indicated by the arrows 96 and 96'.

As the layers of fibers 12 and 14 build up on the respective carriers 16 and 18, the layers impede the further flow of air therethrough. Thus, if the air is to be driven through the layers at the same rate at different portions of the path of the carriers through the forming chamber 20, the pressure differential forcing the air through the carriers 16 and 18 and the respective forming layers 12 and 14 must increase in the direction of travel of the carriers 16 and 18. This is achieved by separately controlling the air flow through respective suction boxes. Suction is applied to the suction boxes 52, 54, 56 and 58 through a duct 99 by a blower 100. Simlarly suction is applied to the suction boxes 72, 74, 76 and 78 through a duct 101 by a blower 102. At the same time, each of the respective suction boxes 52, 54, 56, 58, 72, 74, 76, and 78 includes a damper 104, 105, 107, 109, 104', 105', 107' and 109', respectively for controlling the rate of flow of air through each of the respective suction boxes. Thus, given a desired rate of movement of the carriers 16 and 18, the blowers 25 and 30 and openings 34 may be adjusted to provide an appropriate air velocity within the chamber 20 to provide components of air flow in the direction of movement of the carriers 16 and 18 about equal to the speed of the carriers. At the same time, the blowers 100 and 102 may be driven to provide a proper degree of vacuum within the ducts 99 and 101, whereby adjustment of the dampers substantially equalizes the flow of air along the length of the respective carriers 16 and 18 as the carriers move through the forming chamber 20 over the respective suction boxes.

While the apparatus as thus far described works well at lower speeds, as the apparatus is driven faster and faster, there is less stability to the forming of the layers 12 and 14, and peaks 111 and valleys 106 are produced in the layers. This is particularly true where the layers 12 and 14 are laid down in discrete units, for in such cases, there is no layer laid down at all in the interval between units, and the fibers driven against the respective carriers 16 and 18 in these regions move back into the air stream, disrupting the forming layers, particularly at the edges of the deposited unit. This is illustrated in FIG. 2, which also illustrates the means by which the unevenness of the deposition may be relieved.

Removal means 108 is provided at the exit end of the forming chamber 20 to remove any excess fibers as may be deposited on the carriers 16 and 18. This removal means includes a snout 110 adjacent the nip between the rolls 38 and 62. The snout includes a septum 112 and walls 114 and 116 which define openings 118 and 120 through which air is sucked by a blower 122. The openings 118 and 120 are made relatively narrow to assure the flow of air at a relatively high velocity. The walls 114 and 116 are disposed relatively close to the tops of formed fiber layers 12 and 14 to provide a rush of air over the exposed surfaces of these layers. This does two things; it shears fibers from the surfaces of the layers, and it entrains the fibers in the air stram removed through the air removal means 108. The position of the snout 110 and the flow of air may be adjusted empirically to provide the desired result, that is, the peaks should be removed from the layers 12 and 14, without unnecessarily removing other fibers. This is facilitated by the use of suction at the rolls 38 and 62 under the carriers 16 and 18 in the region of the openings 118 and 120. This assures the retention of the underlying portions of the layers 12 between 14 as the peaks are sheared off. Further, for the same purpose, the suction boxes 58 and 78 are extended under the respective carriers 16 and 18 up to the suction provided by the rolls 38 and 62. Because the deposited fibers impede the flow of air through the deposited layers, the fibers at the peaks 111 are less tightly held to the respective carriers. This permits the removal means to remove fibers from the peaks 111 preferentially without taking so much away from the valleys 106, making the layers 12 and 14 more uniform. The removed fibers may be returned to the suspension through ducts 124 and 124'.

Various modifications may be made in the apparatus within the scope of the present invention. For example, pads of other shapes may be formed. It may be desirable, for example, to form two uniform layers of constant cross section but of different widths, with the two layers being joined to form a pad of non-uniform cross section. It may alternatively be desirable to form substantially identical flat sheets combined to form a thicker pad or a pad having sides of different qualities. For the latter purpose, advantage may be taken of the fact that the form of the invention illustrated in FIG. 1 includes two separate divellicating units 21 and 21'. The two units, particularly with the central removal means 108, provide a flexible arrangement wherein different sorts of fibers may be disposed on the respective carriers 16 and 18. In disposable diapers, for example, it may be desirable to provide high grade fibers on the layer that will be against the child, while using waste fibers for the underlayer, thus providing a cheaper product of superior appearance, yet having the necessary absorbing qualities.

The thickness of the respective layers depends upon the rate at which the fibers are placed in the air stream. 18 percent dilution is suitable, that is, 0.18 pounds of fiber per pound of air. The apparatus as particularly described was designed for forming diapers on 14 inch wide carriers, utilizing refiners producing 2600 pounds of fibers per hour.

What is claimed is:

1. Apparatus for air laying fibers to form a composite pad comprising wall means defining a forming chamber having an inlet, a plurality of air removal openings, and an outlet, a pair of endless foraminous carriers supported for movement into said chamber, over respective ones of said air removal openings, and out said outlet, means for suspending fibers in air, means for directing said fibers suspended in air into said inlet between said carriers, means for applying pressure differential across said carriers in said chamber to force air from said suspension through said carriers and thence through respective ones of said air removal openings, said carriers blocking the passage of fibers therethrough, whereby respective layers of said fibers build up on said carriers, said carriers being supported within said chamber to converge in their direction of motion to join the facing surfaces of the respective layers to form a composite pad moving from said outlet between said carriers and at the same time substantially to block fibers suspended in air from flowing out of the outlet between said carriers, and fiber removal means adjacent the facing surfaces of said carriers, said fiber removal means comprising a source of reduced pressure, elongated restricted snout means having an inlet disposed contiguous to but spaced apart from and above the situs of convergence of said carriers and extending transversely across substantially the full width of said carriers, means substantially dividing said forming chamber into two portions and connecting said source of reduced pressure to said snout means for pulling air from said chamber across the exposed surface of each of said layers of fibers in the direction of forward movement of said layers at a relatively high velocity that shears excess fibers from the facing surfaces of said layers.

2. Apparatus for air laying fibers as defined in claim 1 and including blocking means for directing air through the respective carriers in different patterns to form respective fiber layers of different cross section.

3. Apparatus according to claim 2 wherein said blocking means comprises means blocking a portion of the foramina of at least one of said carriers whereby carriers, is blocked from flowing therethrough to deposit fibers and fibers falling thereon are freely sheared off.

4. Apparatus according to claim 2 wherein said blocking means confines the flow of air through at least one of said carriers to discrete areas.

5. Apparatus for air laying fibers as defined in claim 1 wherein said means for applying pressure differential across said carriers in said chamber includes means to establish a pressure differential that increases at successive air removal openings in the direction of movement of said carriers through said chamber.

6. Apparatus according to claim 1 including means for maintaining relatively low pressure under said carriers in the region of said removal means to hold underlying portions of said carriers as said surface fibers are removed.

* * * * *